United States Patent
DeTurk

(10) Patent No.: US 10,028,685 B2
(45) Date of Patent: Jul. 24, 2018

(54) DEVICE FOR DETERMINING FAT EXPENDITURE FROM LEVELS OF KETONE BODIES THAT HAVE PASSED THROUGH THE SKIN AND METHODS FOR DETERMINING THE SAME

(71) Applicant: Stephen DeTurk, Center Valley, PA (US)

(72) Inventor: Stephen DeTurk, Center Valley, PA (US)

(*) Notice: Subject to any disclaimer, the term of this patent is extended or adjusted under 35 U.S.C. 154(b) by 209 days.

(21) Appl. No.: 15/071,994

(22) Filed: Mar. 16, 2016

(65) Prior Publication Data
US 2016/0270704 A1    Sep. 22, 2016

Related U.S. Application Data

(60) Provisional application No. 62/218,789, filed on Sep. 15, 2015, provisional application No. 62/192,669, filed on Jul. 15, 2015, provisional application No. 62/177,699, filed on Mar. 20, 2015, provisional application No. 62/135,887, filed on Mar. 20, 2015.

(51) Int. Cl.
| | |
|---|---|
| *A61B 5/1477* | (2006.01) |
| *A61B 5/00* | (2006.01) |
| *A61B 5/0205* | (2006.01) |
| *A61B 5/145* | (2006.01) |

(52) U.S. Cl.
CPC .......... *A61B 5/1477* (2013.01); *A61B 5/0205* (2013.01); *A61B 5/14546* (2013.01); *A61B 5/4866* (2013.01); *A61B 5/4872* (2013.01); *A61B 5/6823* (2013.01); *A61B 5/6824* (2013.01); *A61B 5/6825* (2013.01); *A61B 5/6829* (2013.01); *A61B 5/7278* (2013.01); *A61B 5/742* (2013.01)

(58) Field of Classification Search
None
See application file for complete search history.

(56) References Cited

U.S. PATENT DOCUMENTS 5,817,011 A * 10/1998 Schoendorfer .... A61B 5/14521
600/362

OTHER PUBLICATIONS

Yamada et al. "Wearable skin acetone analyzer and its application in health management," NTT Docomo Technical Journal, vol. 17, No. 2, Oct. 2015, pp. 77-82.
Yamada et al. "Skin-emitted acetone detection toward self-monitoring of fat metabolisms," 17th International Conference on Miniaturized Systems for Chemistry and Life Sciences Oct. 27-31, 2013, pp. 1842-1844.

(Continued)

*Primary Examiner* — Brian T Gedeon
(74) *Attorney, Agent, or Firm* — Cozen O'Connor

(57) ABSTRACT

A sensing device having a first and second opening, a first semipermeable membrane having a first surface and a second surface, and a second semipermeable membrane having a third and fourth surface, a ketone body sensor, and a void. The first opening is juxtaposed to the first surface and the second opening is juxtaposed to the third surface. The space between the first and second openings is the void and wherein the ketone body sensor is positioned within the void. Gasses may permeate through the first opening and into the void to contact the sensor and exit the void through the second opening.

20 Claims, 10 Drawing Sheets

(56) References Cited

OTHER PUBLICATIONS

Kao et al. "A sub-ppm acetone gas sensor for diabetes detection using 10nm thick ultrathin InN FETs," Sensors (Basel), 2012, 12(6), 7157-7168.
Purinton et al. "Gor-Tex: An introduction to the material and treatments," The book and paper group annual: The American institute for conservation, vol. 11, 1992, 16 pages.

* cited by examiner

DEVICE FOR DETERMINING FAT EXPENDITURE FROM LEVELS OF KETONE BODIES THAT HAVE PASSED THROUGH THE SKIN AND METHODS FOR DETERMINING THE SAME

PRIORITY

The present application claims the benefit of U.S. Provisional application No. 62/135,887, filed Mar. 20, 2015, U.S. Provisional application No. 62/177,699, filed Mar. 20, 2015, U.S. Provisional application No. 62/192,669, filed Jul. 15, 2015, and U.S. Provisional application No. 62/218,789 filed Sep. 15, 2015.

FIELD OF INVENTION

The present application is generally related to devices suitable for detecting ketone bodies released from the skin and methods for determining the level of fat breakdown based on measured levels of ketone bodies.

BACKGROUND OF INVENTION

Wearable physiological detection sensors are commonly used to detect any number of physiologically relevant data, including but not limited to: heart rate, blood oxygenation, movement, and respiratory rate. These sensor devices were once most commonly associated with static workout machines, such as treadmills, stair climbers, bicycles, elliptical, rowing machines, and the like, however, sensing devices are now ubiquitous in many mobile electronic devices and wearable devices and are no longer required to be tethered to a static exercise machine. For example, most smart phones have a motion or step counter and, many wearable devices assist individuals with measuring their movement, heart rate, and other physiological components during the day and allow individuals to track, store, and mine physiological data throughout the day, or over weeks, months or years. Furthermore, these devices allow for synching of data from one or more sensors and activities, which allows for a greater evaluation of the physiological profile of the user with certain applications and software.

A common feature on static exercise machines is a program to assist a user with reaching and maintaining a target heart rate over a pre-determined amount of time. The target heart rate is often cited as 60% to 75% of maximum heart rate for a "fat-burning zone" and 75% to 85% of maximum heart rate in the so called "aerobic" workout zone. Accordingly, many workout machines, in conjunction with a heart rate monitor, increase or decrease resistance or otherwise modify the exercise program to maintain heart rate within a certain range. Thus, these programs seek to guide users to a certain heart rate based on the age and/or weight of the individual to assist with greater fat loss or aerobic workout, as these "fat burning zones" have not proven to effectively burn greater amounts of fat in all users than higher intensity workouts.

However, the ranges utilized by these programs, specifically the "fat-burning zone," do not necessarily correlate with actual fat burning. Instead, these programs provide users with a program to maintain a particular intensity, usually at a lower heart rate than maximum, and thus corresponding to a reduction in caloric expenditure during the exercise activity as compared to a program aimed at the "aerobic" range. Therefore, lower intensity results in lower caloric burn and thus may not be appropriately aiding the user in burning more fat or more calories as intended.

Ultimately, breakdown of fat and expenditure of calories occur when an individual depletes free energy sources and requires the use of stored fat for metabolic processes. Indeed, the body requires food sources as energy to function. Specifically, certain forms of carbohydrates and glucose provide for a general fuel in cell metabolism. A benefit of carbohydrate or glucose based energy sources is that they are generic, in that they can be metabolized by any cell. Glucose is a readily available energy source and can be obtained directly from food ingested and digested by the body. Furthermore, glucose can be generated by breaking down other carbohydrates within the body when fuel is needed. As the human body cannot constantly process and digest food from the stomach and intestines, it is imperative that some sources of energy can be stored to provide energy for necessary metabolic function.

The body stores certain reserves of energy, such as glycogen and as fat, to maintain sufficient energy reserves for metabolic function. In humans, glycogen is made and stored primarily in the cells of the liver and the muscles, where it is hydrated with three or four parts water. Fats are held in adipose tissue, and ultimately make up the primary storage of energy in the body. Both types of stored energy can be broken down by the body and utilized when the body needs fuel for metabolism.

In the mammalian body, when glycogen reserves are depleted, glucose can be obtained from the breakdown of fatty acids in the liver by the process of beta oxidation to produce ketone bodies for fuel. During fasting, strenuous exercise, or in persons with low glucose levels, fatty acids therefore can be used as a direct source of energy. The byproduct of fatty acids being utilized for energy are ketone bodies. Ketone bodies consist of molecules of acetone, acetoacetic acid and beta-hydroxybutyric acid. The human body can use two of these, acetoacetic acid and beta-hydroxybutyric acid directly, but cannot directly use acetone as a source of energy. Acetone is only partially metabolized in the body, for example by CYP2E1, but it is often eliminated from the body via sweat or urine. Therefore, Acetone is recognized as a byproduct of fat breakdown in the body.

SUMMARY OF INVENTION

The present invention is a wearable device suitable for positioning on the skin of a user, comprising an encasement having a first and second opening, a first semipermeable membrane adjacent to a first opening and a second semipermeable membrane adjacent to a second opening, wherein said first and second semipermeable membranes are permeable to the passage of ketone bodies but not of liquid water; wherein the device further comprises a ketone sensor comprising Indium Nitride and nanoparticles of platinum coating the sensor; and a microprocessor; wherein ketone vapors flow through the first semipermeable membrane through a first opening and contact the sensor, before exiting through the second opening and out the second semipermeable membrane.

A further embodiment is directed to a device comprising an encasement having a plurality of openings adjacent to a void, and positioned within said void is a ketone body sensor comprising an Indium Nitride semiconductor with a coating of Platinum Nanoparticles, a semipermeable membrane, and comprising openings near the sensor allowing for dissipation of ketone bodies; wherein the semi-permeable membrane is permeable to ketone vapors, wherein said ketone vapors pass through the openings and into the void, wherein the vapors can contact the sensor; where after the vapors pass out of the void through a second opening and through a second semipermeable membrane and out of the device.

Another embodiment is directed to a sensing device comprising: a first and second opening; a first semipermeable membrane comprising first surface and a second surface and a second semipermeable membrane comprising a third and fourth surface; a ketone body sensor; and a void; wherein said first opening is juxtaposed to said first surface and said second opening is juxtaposed to said third surface; where a space between said first and second openings is said void and wherein said ketone body sensor is positioned within the void; wherein gasses may permeate through said first opening and into said void to contact said sensor and exit said void through said second opening.

In another embodiment a device for measuring acetone gasses released from the skin of a mammal is provided having an encasement comprising a plurality of openings on a bottom face, and a plurality of openings on adjacent faces, a first and second semipermeable membrane, a void, and a ketone sensor; wherein said first semipermeable membrane is positioned juxtaposed to said bottom face and wherein said second semipermeable membrane is juxtaposed to said openings on adjacent faces; wherein, between said first and second semipermeable membranes is defined the void and positioned within said void is said ketone sensor.

A method of measuring ketone bodies crossing the skin of a mammal is also provided by performing the steps of attaching a device to the skin of a mammal, wherein said device comprises; an encasement comprising a plurality of openings on a bottom face, and a plurality of openings on adjacent faces, a first and second semipermeable membrane, a void, and a ketone sensor; and wherein said first semipermeable membrane is positioned juxtaposed to said bottom face and wherein said second semipermeable membrane is juxtaposed to said openings on adjacent faces; wherein, between said first and second semipermeable membranes is defined the void and positioned within said void is said ketone sensor; detecting acetone gasses being released from the skin of said mammal with said sensor; determining the amount of acetone being released from the skin of said mammal; and displaying the measured amount of ketone bodies crossing the skin on a display on said device.

DETAILED DESCRIPTION OF THE EMBODIMENTS

Figure 1:
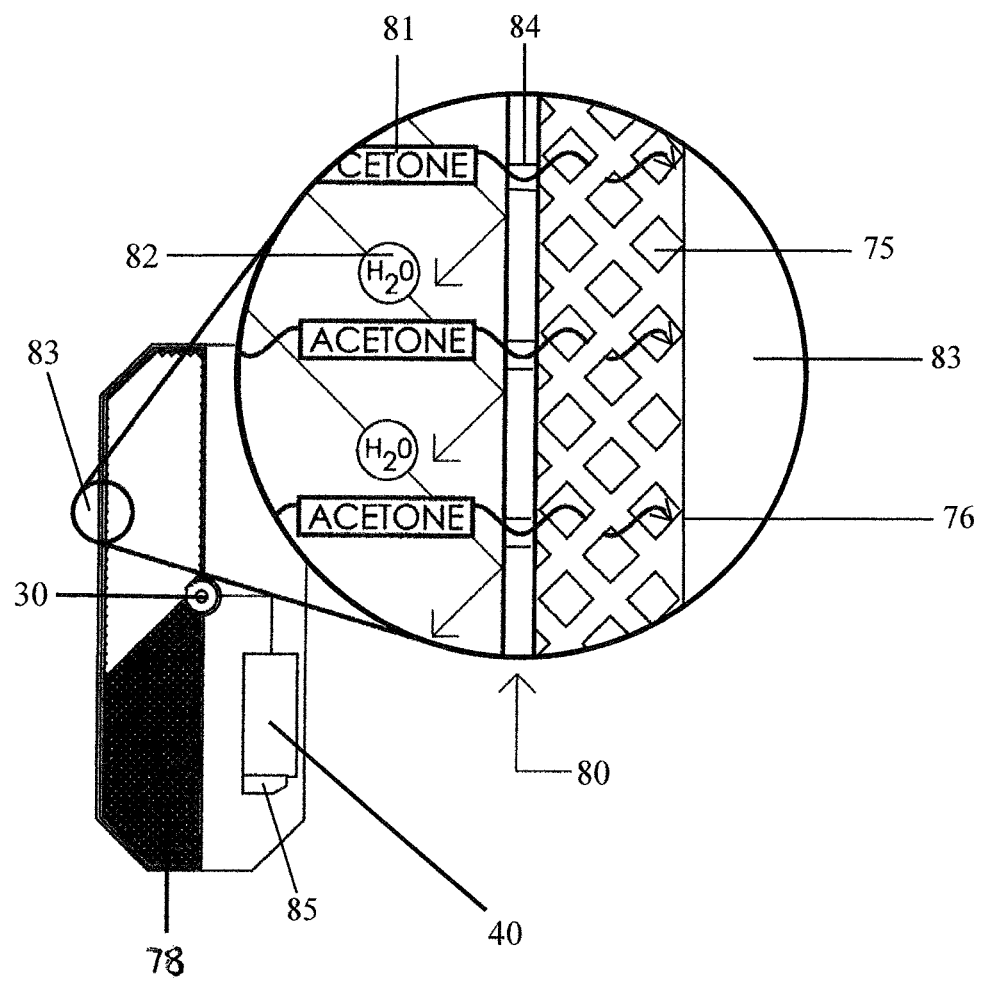
FIG. 1 depicts a cross-section and a detail view of the interface at the point of the semi-permeable membrane, which provides for acetone to pass through, but repels water.

A wearable acetone detection device as described in the embodiments herein is particularly directed to measuring acetone, a ketone body, through the expiration of ketone bodies, i.e. molecules of acetone, acetoacetic acid and beta-hydroxybutyric acid, as vapors from skin. In its most general form, the device comprises a casing that comprises a plurality of openings in a portion of the exterior wall between the outside and a void inside said exterior wall, and comprising a semi-permeable membrane positioned adjacent to said openings so as to selectively prevent the passage of liquid materials through the openings. The device is worn against the skin of an individual, and as water vapors, ketone body vapors, and liquids, including sweat, water, salts, etc. are in contact with the semi-permeable membrane, acetone will permeate, by diffusion, through the semi-permeable membrane, while water will be prohibited from entry. The acetone vapors, travel through the semi-permeable membrane and through the openings in the casing to a void within the casing. Within the void is positioned at least one sensor, which, in combination with a microprocessor, measures the amount of acetone present, and then the acetone passes through a second opening in the casing and back through a second semi-permeable membrane and away from the device. The at least one sensor is connected to a microprocessor and can then display any number of calculations from the sensor on the display on the exterior side of the casing.

In certain embodiments, the level of acetone can also be transmitted from the wearable device to a second device, either through a wired connection or preferably through one of several wireless data transfer as known to one of ordinary skill in the art, including Wi-Fi, short wave radio, Bluetooth among some non-limiting examples. By use of a microprocessor, the device can suitably make any number of calculations related to the level of acetone measured by the sensors. This may be a raw measurement of acetone in parts per million, the fat burned per unit of time, the fat burned during a workout, etc. It may also be suitable to include additional sensors on the wearable device, including a heart rate monitor, respiratory monitor, temperature sensor, step counter, and the like. The microprocessor can utilize each of the measured components to provide for a comprehensive view of the physical activity and the calories and the fat burned. Furthermore, the measured physiological data can be exported to additional devices for greater data mining and calculations for the user.

The wearable device comprises a suitable rechargeable battery within the encasement, which can be appropriately charged by an electrical source. Other sources of energy, such as suitable automatic movements known to one of skill in the art are also suitable in certain preferred embodiments, such as those used in the watch industry, or use of solar or other energy sources.

In preferred embodiments, the wearable acetone detection device is worn against the skin of a user, for example on the arm, leg, or chest of the person. Appropriate length straps are connected to the device based on the location to be worn. The device is worn against the skin, with the skin facing side of the device comprising a plurality of openings in the encasement. Adjacent to the plurality of openings is a semi-permeable membrane, wherein the vapors from the skin pass through the semi-permeable membrane and through the openings in the encasement, but liquids do not pass through.

In certain preferred embodiments, the wearable device comprises at least one platinum coated Indium Nitride (InN) sensor positioned within a void in the encasement, wherein acetone molecules flow past the sensor via diffusion from the skin, through a semi-permeable membrane, through an opening in the encasement of the wearable device, where the acetone contacts the sensor, before its removal from the void and out through a second opening and through a second semi-permeable membrane.

A particular embodiment is depicted by FIG. 1, which provides for a detail of a cross-section view of a wearable acetone sensing device. The circled (magnified) portion of the figure provides for a visual of the boundary between the encasement and the semi-permeable membrane 80. Indeed, the semi-permeable membrane 80 has a first surface and a second surface, with the distance between, being the thickness of the membrane. The first surface is open to the air, wherein the second surface is in direct contact with the first surface of the encasement. The semipermeable membrane is permeable to gasses, such as acetone, but does not allow for entry of a liquid such as water. Suitable membranes include polymers of polytetrafluoroethylene. However, other suitable materials include a variety of polymers of silanized aluminia, and other materials and polymers that prevent passage of liquid water, but allow for the passage of gasses, such as the acetone being measured by the sensing device.

The encasement has a first surface that is either in contact with the semi-permeable membrane 80, or is in contact with the air, and a second surface that is open to an internal void 83. The distance between the two encasements surfaces is the thickness of the encasement. The encasement has an outer face 78, and the encasement is preferably about 0.1 to about 2 mm in thickness and is made of a suitable plastic, polymer, or metallic material. In certain embodiments, the encasement may comprise a first material that is adjacent to the membrane, and a second material that is not in contact with the membrane. In certain embodiments a metallic microlattice is suitably used for its ability to transfer and dissipate heat away from the sensors disposed of within the encasement.

Figure 3A:
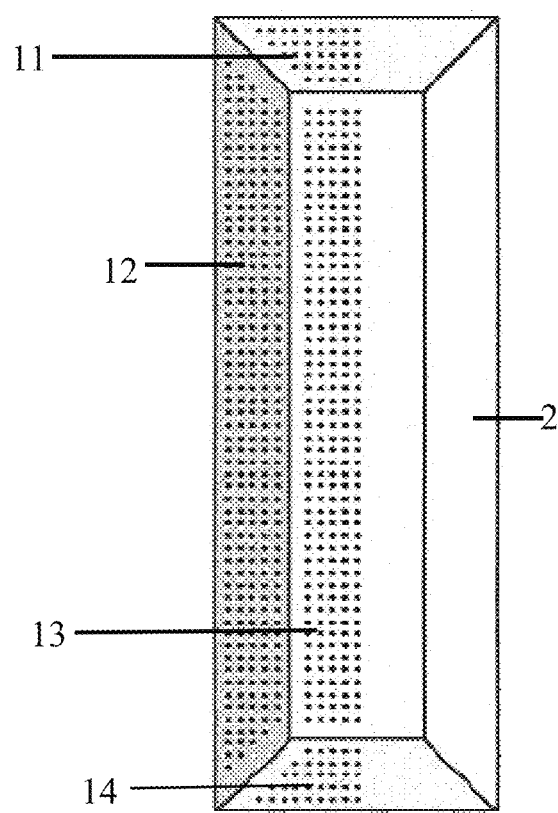
FIGS. 3A and 3B depict the left and right side profile of a wrist sensor.

The semi-permeable membrane 80 will only be present in areas where the encasement 76 contains openings 75 between the first and second surface of the encasement. For example, FIG. 3A depicts portions with "dotted" areas and non-dotted areas. The dotted areas represent the semipermeable membrane. These encasement openings 75, are depicted as having a square shape in FIG. 1, however, the shape of the openings is not material to the invention. The openings 75 are of suitable size to allow for the passage of ketone vapors without being too small to be restrictive to such vapors or too large to provide for weakness of the material. Suitable opening sizes are between 0.001 and 2 mm in any dimension, for example a 0.001-2 mm diameter circle, or a square having lengths of about 1 mm. These openings 75 between the first and second surface of the encasement, therefore allow for the passage of the vapors into the void 83.

Within the void 83 is positioned one or more acetone sensors 30. The sensor is positioned such that the ketone vapors that flow through the skin facing surface contact the sensor 30 and then diffuse out of the void through further openings 75 in the encasement 76.

Within the encasement, a microprocessor 40 is further positioned to process and collect data from the sensor, and to provide content to a display. A battery 85 is further provided to power each of the components, including the sensors, the microprocessor and the display.

Figure 2A:
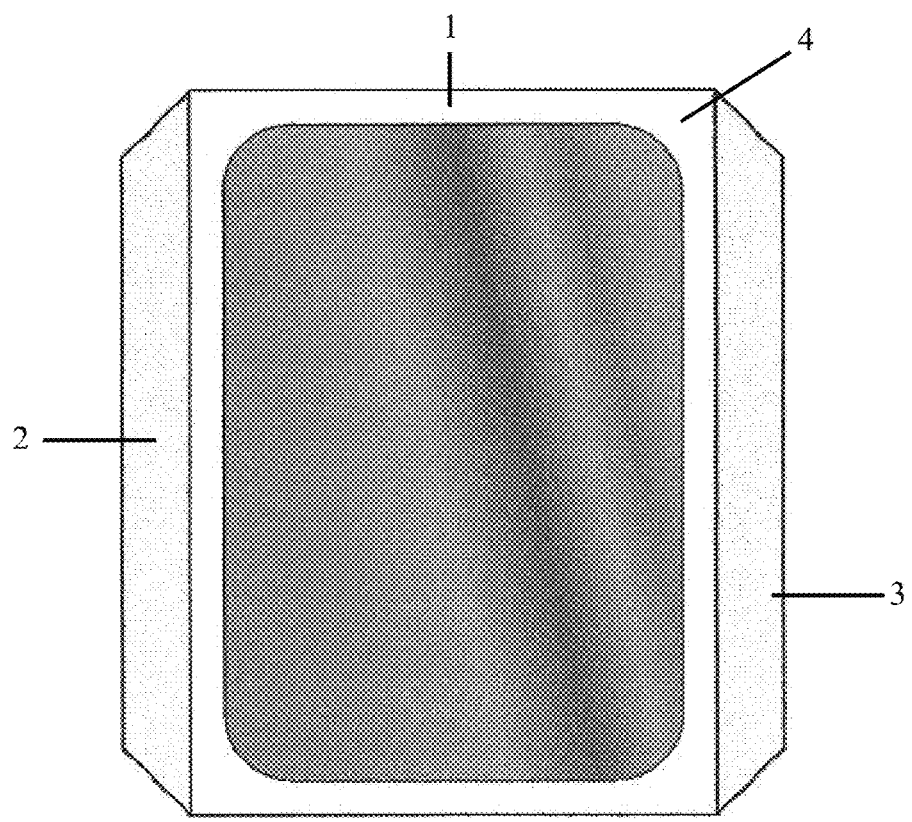
FIGS. 2A and 2B depict the top and bottom of a wrist sensor.
Figure 2B:
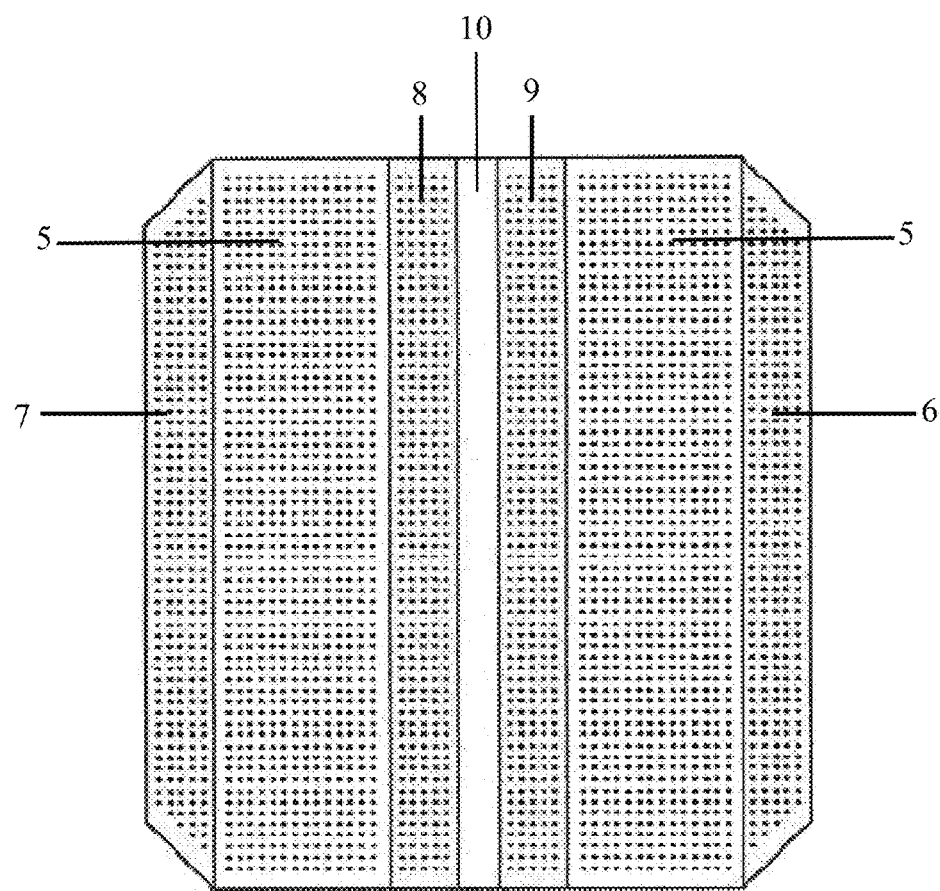

FIGS. 2A and 2B depict an embodiment of the top of the encasement of an acetone detection device having a generally rectangular shape and beveled edges. FIG. 2A depicts a view from top down, showing a display 1, the top panel 4, and a left edge 2 and a right edge 3. The display 1 may be any ordinary screen that provides the ability to display numbers and/or images. Examples of such displays may include LCDs used in common television and display devices. Other suitable displays include OLED, TFT, and other similar display features as known to one of ordinary skill in the art.

FIG. 2B depicts a bottom view of an acetone detection device. The bottom side shows two flat surfaces 5 having a semi-permeable barrier. The semi-permeable barrier is represented by the dotted portions. As depicted, the dotted portions of features 5, 6, 7, 8, and 9, is a representation of a semi-permeable membrane made of polytetrafluoroethylene. The polytetrafluoroethylene allows for passage of acetone bodies, but prevents the passage of water, among other liquids and gasses. This allows for the semi-permeable membrane to selectively allow passage of the acetone to reach a sensor 30 within the detection device.

Figure 4A:
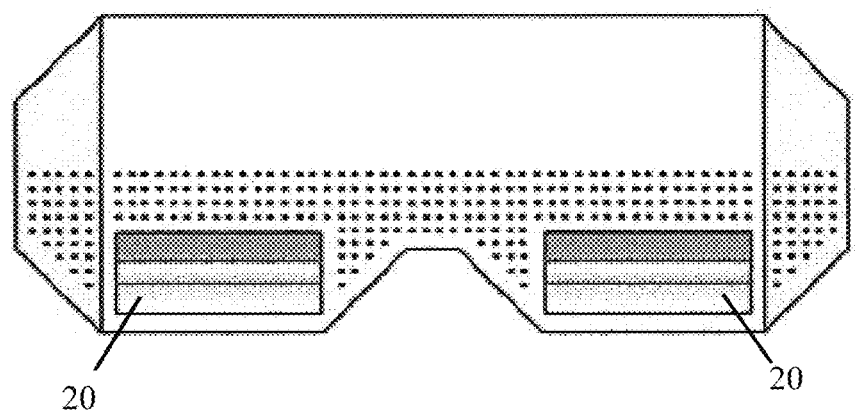
FIGS. 4A-4C depict a cutout view of a wrist sensor from the top and bottom profile, and a perspective view of the component for wrist strap attachment.
Figure 4B:
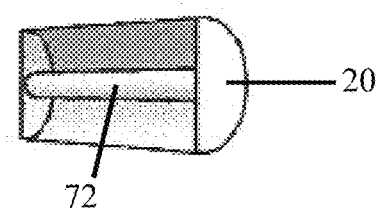

A particular feature of FIG. 2B is the existence of a channel 10 positioned running vertically from top to bottom in a central position. FIGS. 4A and 4B further show that this channel is recessed, and having angular beveled portions between the sides of the channel 10 and the bottom face of the flat surface 5. These left angled bevel 8 and right angled bevel 9, are positioned to allow for acetone to exit the device, and then pass through the channel away from the skin.

Gasses and flow of ketone vapors are intended to pass from the skin through the semipermeable membrane flat surface 5 through the openings 75 in the encasement, and into the void 83. Entry into the void 83 then allows for the vapors to contact with a sensor 30. After contact with a sensor 30, the vapors diffuse away from the sensor 30 and through a further opening in the encasement and out of the device through the surfaces, e.g. 6, 7, 8, and 9. For the surfaces 8 and 9, the central channel 10 then assists in evacuating the gasses from device and away from the skin.

In certain preferred embodiments, the device may further utilize a small fan device positioned to pull vapors into the void, and to expel them from the side surfaces 6, 7, 8, and 9, as well as those the side faces 13 and 17.

Figure 3B:
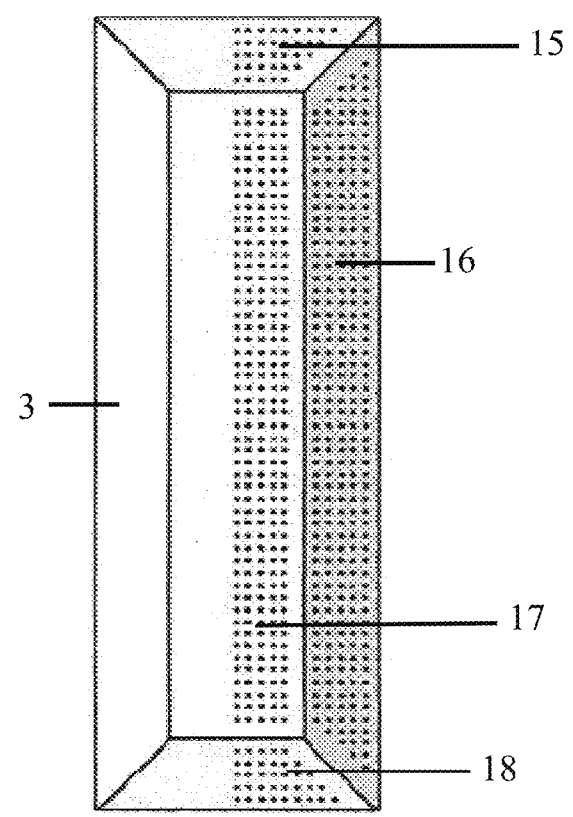

FIGS. 3A and 3B depict the left and right side profiles of the embodiment of FIGS. 2A and 2B. The left side, would be adjacent to the side bevel 2, as is shown in FIG. 3A. Then a flat side face 13 is provided, and having bevels 11 and 14 on the side, and bottom bevel 12 opposing the side bevel 2. FIG. 3B depicts the mirror image of the left side, with a side face 17, being adjacent to the side bevel 3, and further including beveled sides 15 and 18, and bottom bevel 16. All the semipermeable surfaces depicted in 3A and 3B assist with expelling gasses from the device. As is depicted, the semipermeable membrane does not cover the entirety of the encasement. Indeed, in FIG. 3A, only about one-half of the faces 11, 13, and 14 are covered with the semipermeable membrane.

Figure 4C:
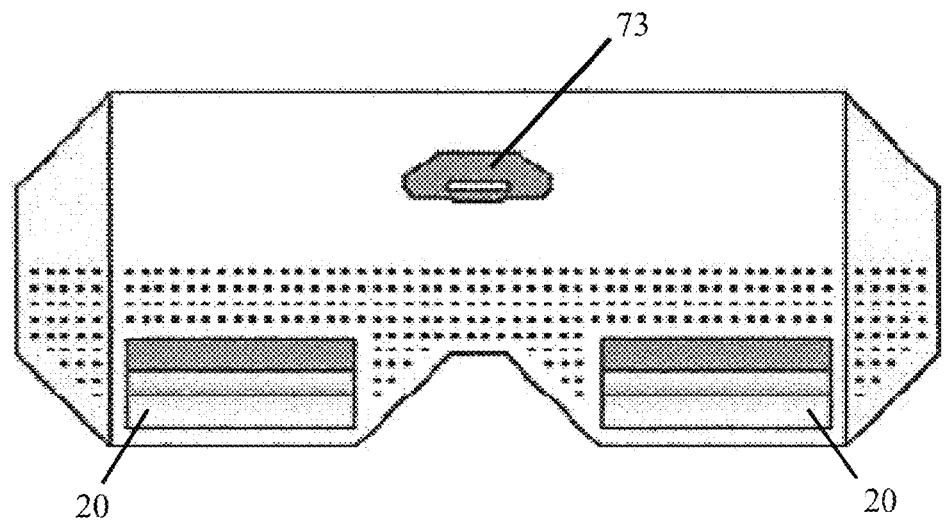

FIGS. 4A and 4C depict an end view from the top and bottom sides. In particular, depicted on 4A and 4C are the strap slots 20, which allow the device to be attached to a band for securing around an arm, leg, or chest. FIG. 4C depicts a perspective view of the strap slot, showing that a pin 72 is secured within an opening, to allow for a band to be secured around the pin 72. This pin 72 may be permanent, or use a removable pin 72, such as a watch pin. Depicted on FIG. 4C, is a charging port 73. A suitable charging port 73 is one of any known micro charging ports like a micro USB, as a non-limiting example of a charging port known to one of ordinary skill in the art. This charging port can also be utilized to download data stored within memory within the device. However, data can also be transmitted to external devices wirelessly, and in such cases, the microprocessor must also include an appropriate attached wireless transmitter.

Therefore, a suitable receiver may be advantageously utilized with the device. The receiver can receive data from the device via a tethered connection or wirelessly transmitted by means known to one of ordinary skill in the art. The receiver can further use a microprocessor to display data, and convert data from the sensors into an output for display on the device or on the receiver, or on a further display device. However, preferred embodiments utilize a display on the device itself, and an embedded microprocessor in the device to receive data from sensors, perform appropriate calculations and to display information regarding the data on the device itself.

Figure 5:
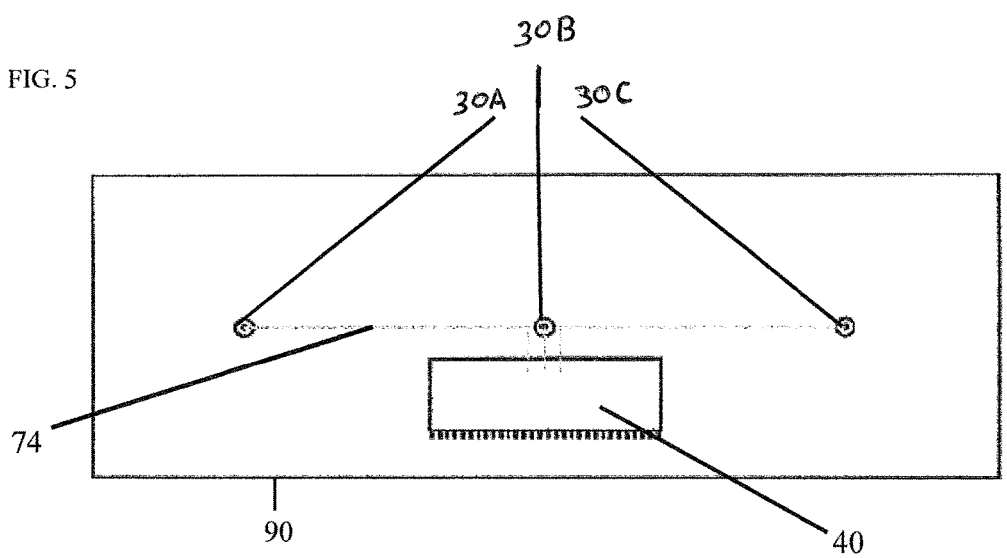
FIG. 5 depicts the internal view of a chest strap and depicting three sensors connected to a centralized microprocessor.

FIG. 5 depicts an embodiment utilizing a middle plate 90. The middle plate 90 provides one embodiment for attaching the sensors 30A, 30B, and 30C within the void 83. These sensors are then electronically interfaced with a microprocessor 40 such as by way of a wire 74 or other technique. In a preferred embodiment, the sensors 30A, 30B, and 30C are platinum coated Indium Nitride (InN) sensors for detecting acetone. The sensors utilizes platinum nanoparticles, which have known catalytic properties facilitating an improved sensor response. However, other suitable sensors may be utilized in certain embodiments as known to one of ordinary skill in the art. For example, one or more of elements 30A, 30B or 30C may be a sensor other than a ketone sensor, such as a heart rate monitor, a respiratory monitor, blood pressure, movement/step counter, or other known sensors. However, at least one sensor is an acetone sensor. Certain sensors may be able to perform multiple tasks. Furthermore, certain sensors may require a contact point with the skin for measurements, and the panels, e.g. on FIG. 7A may include one or more contact points as required for functionality of an encased sensor.

Figure 6A:
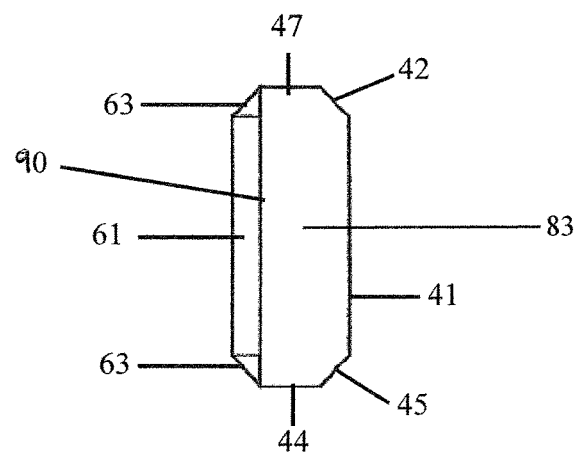
FIGS. 6A and 6B depict a cross-section view of a chest sensor and a top frontal view of a chest sensor.
Figure 6B:
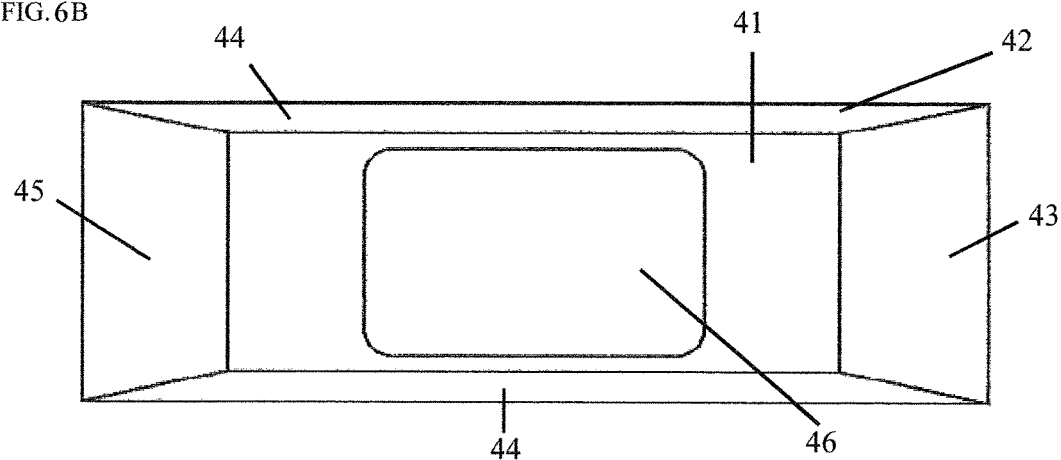

Stacked on top of the middle plate 90, is the top plate depicted in FIG. 6B. The top plate, includes the display opening 46, a top bevel 42, a bottom bevel 44, a top panel 41, and side bevels 45 and 43. A suitable display is positioned within the display opening for visualization of the data collected by the included sensors.

FIG. 6A provides a cross-sectional view of the top plate and shows that the bottom panel 61 and the bottom bevels 63 then connect to the middle plate 90, containing the sensors and the microprocessor. Adjacent to the middle plate 90 is a void 83. In certain embodiments the void 83 may be open to the semi-permeable membrane. In other embodiments, the middle plate 90 can assist with sealing off the void to allow for the sensor to be within the void, but the remaining components of the device secured between the middle plate 90 and the top portion of the device (e.g. FIG. 6B). Therefore, the middle plate 90 need not seal off the void in certain embodiments, but in other embodiments, the middle plate 90 can assist in creating the void space.

Figure 7A:
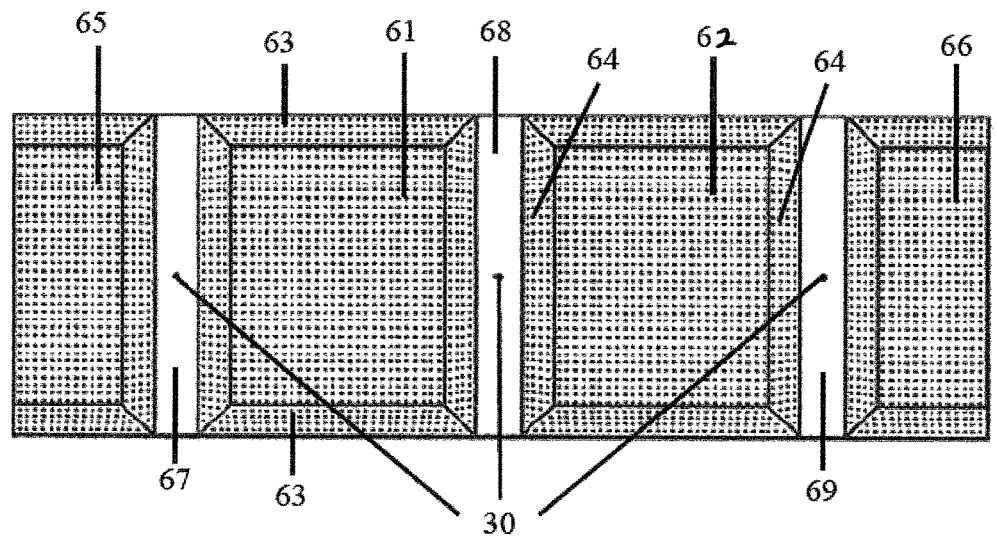
FIGS. 7A and 7B depict the skin facing side of a chest sensor, which depicts the sensors situated within channels and a cross-section view of an embodiment of the device.
Figure 7B:
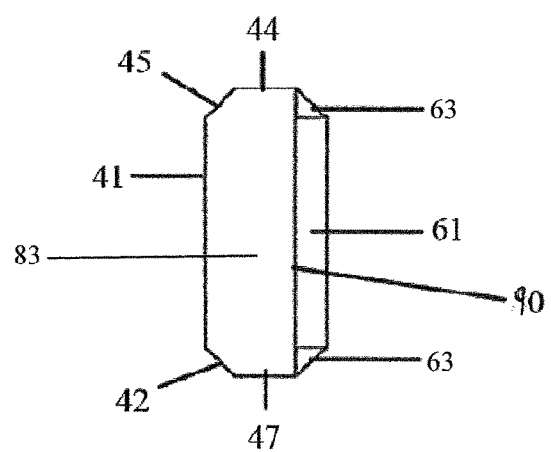

FIG. 7A depicts a bottom view of an embodiment of an acetone sensor, wherein there are four different bottom panels, 61, 62, 65, and 66. Each of the bottom panels is covered with a semi-permeable material, and is intended for contact with the skin. The sensors, 30 are shown positioned in channels 67, 68, and 69, for purposes of their location within the device. FIG. 7B, like FIG. 6A, shows a cross-section of an embodiment of the device.

Figure 8:
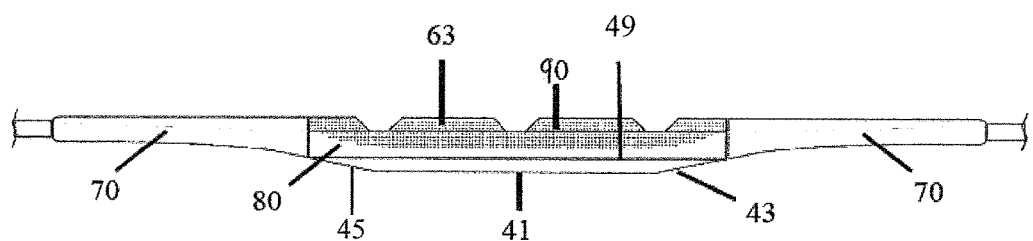
FIG. 8 depicts a side profile image of a chest sensor.
Figure 9:
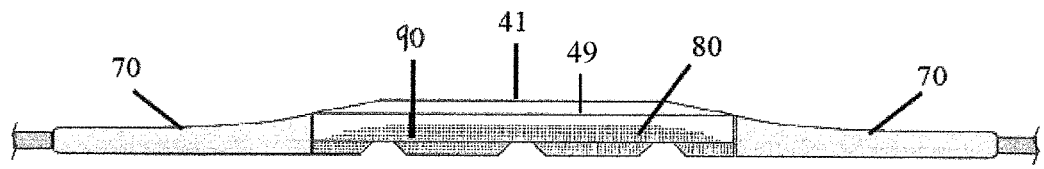
FIG. 9 depicts the opposing side view from FIG. 8.
Figure 10:
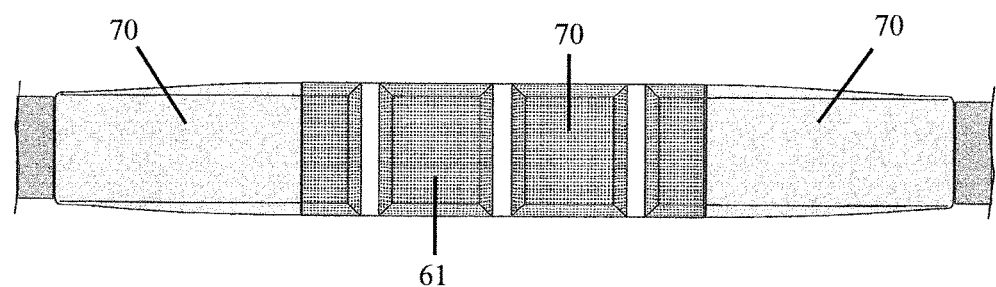
FIG. 10 depicts a skin facing side of a chest sensor embodiment and attached strap assembly.
Figure 11:
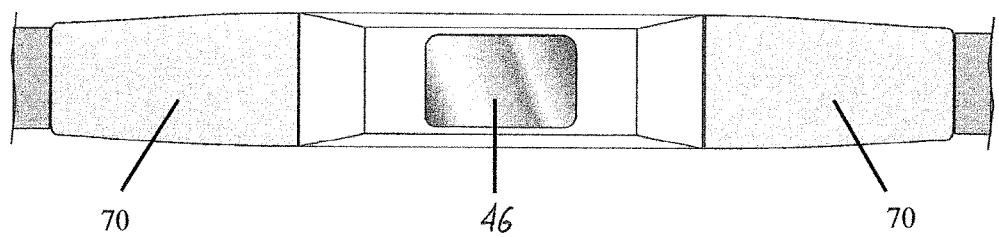
FIG. 11 depicts a top view of a chest sensor and strap assembly.

FIG. 8 depicts a side profile view of a chest strap embodiment. The straps 70 are attached to the body portion of the device, and the skin contacting plates, would be positioned on the top view. The straps may be elastic or inelastic material that can be appropriately secured around a body or appendage so as to enable the device to be in contact with a skin surface. The beveled plates, e.g. 63 are viewable from the side profile. Feature 49 is also depicted, which is the bottom of the top plate, and creates a central section 80 where the battery, circuitry, microprocessor, memory, and the like may be advantageously stored. FIG. 9 depicts the opposing view. FIG. 10 depicts a bottom plan view, with the skin facing side up and FIG. 11 depicts a top plan view of a chest strap embodiment, with the non-skin side facing up.

In certain embodiments, the semi-permeable membrane is positioned between the inner surface of the encasement and the void. Thus, in certain embodiments, the openings in the encasement are in contact with the skin, wherein the vapors pass into these openings and then enter the void by passage through the semi-permeable membrane. In certain embodiments, the semi-permeable membrane may comprise a single layer membrane. In other preferred embodiments, the semi-permeable membrane is made up of two or more layers, wherein the layers are in direct contact with one another, such that a first surface of one layer is in direct contact with a first surface of another layer.

In other preferred embodiments, a semi-permeable membrane is positioned on each side of the encasement, such that a first membrane is positioned outside the encasement and is intended to contact the skin, and a second semi-permeable membrane is positioned with a first surface in contact with the internal face of the encasement, and a second surface open to the void. This provides for a membrane void with the space of the openings in the encasement.

The device is intended for continuous use for measuring ketone bodies on the skin surface of a mammal. Therefore, in preferred embodiments, the mammal includes rodents, cats, dogs, swine, bovine, equine, caprinae, and primates. For example, the device may be advantageously used to determine the rate of fat burn in a model species, or used as a work-out of data device for humans. Other suitable uses may be for detecting ketone bodies exiting the skin of a mammal, for optimizing fat burn in a mammal among other non-limiting examples of the intended use of the device.

Accordingly, the disclosure contemplates preferred methods for determining the amount of ketone bodies crossing the skin of a mammal. Ketone bodies produced within a mammalian body produce acetone which is expressed and evacuated, in part, through the skin. The described devices herein, comprises a device having openings in the base of the device which is in juxtaposition to the mammal's skin, wherein acetone vapor passes through a semipermeable membrane on the device and permits vapors to pass through the semipermeable membrane but not water. Within the device, a sensor detects acetone and an attached microprocessor coverts the signal generated from the sensor and coverts this signal to a display.

Further methods comprise determining the rate of fat being processed in a mammal comprising; applying a device to the skin of said mammal, wherein said device comprises an acetone sensor capable of detecting acetone vapors being expelled from the skin of said mammal; measuring the acetone from said mammals skin; calculating the rate of fat being processed in said mammal based on the measurement of acetone from said sensor.

A further method is directed to optimizing the rate of fat burn during an exercise activity in a mammal comprising applying a device to the skin of said mammal, wherein said device comprises a sensor positioned between a first and second semipermeable membrane; measuring the amount of acetone contacting said sensor over a rate of time; modifying said exercise program to increase or decrease activity to increase the rate of fat burn.

A further method is directed to measuring acetone concentrations from the skin of a human comprising measuring acetone with a platinum coated Indium Nitride (InN) sensor juxtaposed between a first and second semi-permeable membrane.

What is claimed is:

1. A sensing device comprising:
    a. a first opening and a second opening;
    b. a first semipermeable membrane comprising a first surface and a second surface and a second semipermeable membrane comprising a third surface and a fourth surface;
    c. a ketone body sensor; and
    d. wherein said first opening is in contact with said first surface and said second opening is in contact with said third surface for forming a void therebetween, and wherein said ketone body sensor is positioned within the void; wherein gasses may permeate through said first opening and into said void to contact said sensor and exit said void through said second opening.

2. The sensing device of claim 1, having a housing shaped for contacting the skin of a mammal; wherein said second surface may be suitably placed against the skin of said mammal.

3. The sensing device of claim 2, wherein said mammal is a primate.

4. The device of claim 2, wherein housing is suitable for contacting a body part selected from the group consisting of: a hand, wrist, arm, chest, torso, leg, foot, and ankle.

5. The device of claim 1, further comprising a receiver component suitable for electronic connection between the device and said receiver component.

6. The device of claim 1, wherein said semipermeable membrane is made up of at least one layer of polytetrafluoroethylene.

7. A device for measuring acetone gasses released from the skin of a mammal comprising:
    a. an encasement comprising a plurality of openings on a bottom face, and a plurality of openings on at least one face which is adjacent to the bottom face, a first semipermeable membrane, a second semipermeable membrane, and a ketone sensor;
    b. wherein said first semipermeable membrane is positioned in contact with said bottom face and wherein said second semipermeable membrane is positioned in contact with said openings on an adjacent faceto said bottom face; wherein, said first and second semipermeable membranes are positioned on said bottom face and adjacent face, respectively, to define a void therebetween, and wherein said ketone sensor is positioned in the void.

8. The device of claim 7, further comprising a microprocessor and a display, wherein said microprocessor processes data received from said sensor and provides an output to said display.

9. The device of claim 7, wherein said first and second semipermeable membranes are made up of at least two layers.

10. The device of claim 7, wherein said semipermeable membrane is made up of at least one layer of polytetrafluoroethylene.

11. The device of claim 7, wherein said sensor is a platinum coated Iridium Nitride sensor.

12. The device of claim 11, wherein said sensor further comprises platinum nanoparticles.

13. The device of claim 7, wherein said encasement is a metallic microlattice, wherein said microlattice is connected to said sensor for dissipation of heat from said sensor.

14. A method of measuring ketone bodies crossing the skin of a mammal, comprising:
    a. attaching a device to the skin of a mammal, wherein said device comprises; an encasement comprising a plurality of openings on a bottom face, and a plurality of openings on adjacent faces, a first and second semipermeable membrane positioned adjacent each other to define a void therebetween, and a ketone sensor; and wherein said first semipermeable membrane is positioned in contact with said bottom face and wherein said second semipermeable membrane is in contact with said openings on adjacent faces; wherein, said ketone sensor is positioned in the void;
    b. detecting acetone gasses being released from the skin of said mammal with said sensor;
    c. determining the amount of acetone being released from the skin of said mammal; and
    d. displaying the measured amount of ketone bodies crossing the skin on a display on said device.

15. The device of claim 14, wherein said device further comprises a fan to pull gasses across the sensor and to expel said gasses from said void.

16. The device of claim 14, wherein said sensor is a Platinum coated Indium Nitride sensor.

17. The device of claim 14, comprising the further step of transmitting the amount of acetone being released from the skin of said mammal to a receiver that is wirelessly connected to said device.

18. The device of claim 14, wherein said device encasement is a metallic microlattice, and wherein said sensor is connected to said metallic microlattice.

19. The device of claim 14 further comprising at least one further sensor selected from the group consisting of: heart rate, blood pressure, and step counter.

20. The device of claim 14 wherein said semipermeable membrane is made up of at least one layer of polytetrafluoroethylene.

* * * * *